(12) United States Patent
Volpicelli et al.

(10) Patent No.: US 9,481,686 B2
(45) Date of Patent: Nov. 1, 2016

(54) PROCESS FOR PREPARING ENANTIOMERICALLY ENRICHED OXAMIDES

(71) Applicant: Zach System S.P.A., Bresso (IT)

(72) Inventors: Raffaella Volpicelli, Vicenza (IT); Antonio Nardi, Gambellara (IT); Mauro Andretto, Noventa Vicentina (IT); Ilaria Munari, Vicenza (IT); Roberto Brescello, Abano Terme (IT); Anna Smaniotto, Treviso (IT); Livius Cotarca, Cervignano del Friuli (IT); Massimo Verzini, Caldiero (IT)

(73) Assignee: ZACH SYSTEM S.P.A., Bresso (MI) (IT)

( * ) Notice: Subject to any disclaimer, the term of this patent is extended or adjusted under 35 U.S.C. 154(b) by 0 days.

(21) Appl. No.: 14/412,450

(22) PCT Filed: Jun. 28, 2013

(86) PCT No.: PCT/EP2013/063644
§ 371 (c)(1),
(2) Date: Jan. 1, 2015

(87) PCT Pub. No.: WO2014/005943
PCT Pub. Date: Jan. 9, 2014

(65) Prior Publication Data
US 2015/0191485 A1    Jul. 9, 2015

(30) Foreign Application Priority Data

Jul. 3, 2012 (IT) ............................. MI2012A1165

(51) Int. Cl.
*C07D 495/04* (2006.01)

(52) U.S. Cl.
CPC .................. *C07D 495/04* (2013.01)

(58) Field of Classification Search
CPC .................................................. C07D 495/04
See application file for complete search history.

(56) References Cited

U.S. PATENT DOCUMENTS 4,863,922 A    9/1989    Baldwin et al.

FOREIGN PATENT DOCUMENTS

| EP | 1918293 | 5/2008 |
| WO | 2008135770 | 11/2008 |
| WO | WO 2011101704 A1 * | 8/2011 |
| WO | WO 2012120086 A1 * | 9/2012 |

OTHER PUBLICATIONS

Blacklock T., et al. "An Enantioselective Synthesis of the Topically-Active Carbonic Anhydrase Inhibitor MK-0507: 5,6-Dihydro-(S)-6-Methyl-4H-Thienoa2,3-Buthiopyran-2-Sulfonamide-7,7-Dioxide Hydrochloride", Journal of Organic Chemistry, ACS, US, vol. 58, No. 7, Jan. 1, 1993.
Written Opinion of PCT/EP2013/063644 of Aug. 12, 2013.
Search Report of PCT/EP2013/063644 of Aug. 12, 2013.

* cited by examiner

*Primary Examiner* — Samantha Shterengarts
*Assistant Examiner* — Matt Mauro
(74) *Attorney, Agent, or Firm* — Silvia Salvadori, P.C.; Silvia Salvadori (57) ABSTRACT

The present invention relates to a chiral oxamide of formula (I) useful as an intermediate in the preparation of dorzolamide, and to the preparation thereof. The invention also relates to the preparation of dorzolamide, to the hydrochloride salt thereof, and to the active ingredient contained in a drug useful in the treatment of glaucoma, by means of the intermediate of formula (I).

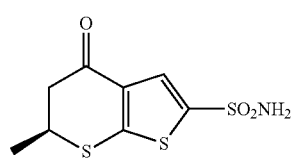

(I)

16 Claims, 2 Drawing Sheets

Figure 1: XRPD of Form 1

Figure 2: XRPD of Form 2

PROCESS FOR PREPARING ENANTIOMERICALLY ENRICHED OXAMIDES

This application is a U.S. national stage of PCT/EP2013/063644 filed on 28 Jun. 2013, which claims priority to and the benefit of Italian Application No. MI2012A001165 filed on 3 Jul. 2012, the contents of which are incorporated herein by reference in their entireties.

The present invention relates to a compound of formula (I)

(I)

useful as an intermediate in the preparation of the active ingredient dorzolamide hydrochloride, and to a process for the preparation thereof The invention also relates to the preparation of dorzolamide hydrochloride by means of said intermediate of formula (I).

MEASUREMENT METHODS

The graphs obtained by means of the use of the X-ray powder diffraction (XRPD) technique were obtained with a diffractometer and were established using a Bruker D8 Advance diffractometer with Bragg-Brentano geometry under the following conditions:
X-ray tube: copper
Radiation used: K($\alpha$1) and K($\alpha$2)
Voltage and current of the generator: 40 kV, 40 mA
Detector: PSD
Step size: 0.015
Time per step: 0.5 seconds
Initial and final 2$\theta$ angular value: 3.0°-40.0°

DETAILED DESCRIPTION OF THE INVENTION

European patent EP 296879 describes compounds effective as inhibitors of carbonic anhydrases, including dorzolamide, of formula:

The hydrochloride salt of dorzolamide is the active ingredient contained in the proprietary medicinal product Trusopt®, which is used in the form of ophthalmic drops in the treatment of patients suffering from glaucoma. The ingredient dorzolamide hydrochloride is also combined with the active ingredient timolol maleate in the form of ophthalmic drops in the proprietary medicinal product Cosopt®.

The process for preparing dorzolamide and salts thereof was described for the first time in patent EP 296879 (EP'879). In EP'879, the production of enantiomerically pure dorzolamide requires the use of intermediates that are enantiomeric mixtures, the use of a chromatography column and of a chiral resolving agent in the final phases of synthesis, with a subsequent significant reduction of the reaction yields.

Patent EP 2010544, of the same applicant, refers to an alternative synthesis method that comprises a process for resolving trans racemic (±) (4S,6S;4R,6R)-4-(ethylamino)-5,6-dihydro-6-methyl-4H-thieno-[2,3-b]thiopyran-2-sulfonamide 7,7-dioxide (dorzolamide trans racemate) of formula:

characterised by:
a) reacting said racemate with (1S)-(+)-10-camphorsulfonic acid of formula:

b) obtaining the (4S,6S) enantiomer by selectively precipitating and recovering the relative camphorsulfonic acid salt thereof (dorzolamide camphorsulfonate) of formula:

c) neutralising the dorzolamide camphorsulfonate to obtain dorozolamide and, if desired, transforming the dorzolamide into the hydrochloride salt thereof The trans racemate of dorzolamide can, in turn, be prepared in accordance with the prior art teachings, for example by following the steps illustrated below in Schema 1

Schema 1

4-oxo-solfuro $\xrightarrow[\text{Step 1}]{\text{H}_2\text{O}_2 \\ \text{Na}_2\text{WO}_4\cdot 2\text{H}_2\text{O}}$ pure form on an industrial scale without loss of yield have driven the present inventors to try and find a new process that meets the above-mentioned needs.

In order to therefore increase the productivity of the process and consequently reduce the productions costs of dorzolamide hydrochloride whilst overcoming the above-mentioned drawbacks, the present inventors have prepared an alternative method for the synthesis of dorzolamide, which uses, as raw material, a new compound in which the configuration of the methyl group in position 6 of the 4-oxo-sulfur of Schema 1 is already established in the S configuration.

The present invention therefore firstly relates to a new compound of formula (I):

also referred to hereinafter as dorzo oxamide and useful as an intermediate in the preparation of dorzolamide hydrochloride.

Blacklock et al., J. Org. Chem., 1993, 58, 1672-1679 have already attempted to obtain the compound of formula (I) from the raw material available on the market of formula (III):

following the synthesis method illustrated in Schema 2:

Schema 2

X = S composto di formula (III),
X = SO$_2$

X = S composto di formula (II),
X = SO$_2$

Although the above-mentioned synthesis method according to patent EP 2010544 has advantages compared to the method specified in patent EP 296879, it results in a loss in yield however greater than 50% of dorzolamide camphor-sulfonate following resolution of the trans racemate and subsequent isolation of the desired isomer dorzolamide 4S,6S.

The difficulties in specifying a synthetic process that is simultaneously neat, easily implemented and conveniently leads to the production of dorzolamide hydrochloride in a

-continued

More specifically, whereas the chlorosulfonation of the compound of formula (III) occurs without erosion of the enantiomeric excess, the successive amidation leads however to complete racemisation of the product via retro-Michael, even from the corresponding compound in which X=SO$_2$.

Although the lack of success of Blacklock et al. discouraged those skilled in the art from starting from the same raw material in order to obtain the desired compound of formula (I), the present inventors have surprisingly found that the reaction of amidation can be performed still maintaining the high enantiomeric excess of the compound of formula (I), working with suitable technical equipment.

IT is therefore a further object of the present invention therefore also relates to a process for preparing the compound of formula (I) with an enantiomeric excess equal to or greater than 60% comprising the reaction of the compound of formula (II)

with NH$_3$ or salts thereof; said process being characterised in that the reaction is carried out in an acidic or neutral environment.

An acidic or neutral reaction environment is obtained by applying the knowledge of a person of average skill in the art in the light of the teachings provided by the prior art; for example working with a number base equivalents equal to or less than the acid equivalents initially present in solution.

In a specific aspect, in order to obtain the compound of formula (I) with an enantiomeric excess equal to or greater than 60%, one mole equivalent of the compound of formula (II) is reacted with an amount between 2 and 3 mole equivalents of NH$_3$.

The enantiomeric excess with which the compound of formula (I) is obtained is preferably equal to or greater than 70%, more preferably equal to or greater than 80%, and in particular is equal to or greater than 90%.

In accordance with the present invention, the term NH$_3$ includes NH$_3$ gas, NH$_3$ in organic solution and NH$_3$ in aqueous solution, otherwise known as NH$_4$OH.

In accordance with the present invention, the salts of NH$_3$, otherwise known as ammonium salts, can be selected for example from (NH$_4$)$_2$CO$_3$, NH$_4$(HCO$_3$) and CH$_3$COONH$_4$.

The process according to the present invention can be carried out, for example, in an organic solvent, such as methanol, ethanol, isopropanol or dioxane, in the presence of a polar or non-polar aprotic solvent, such as acetone, tetrahydrofuran (THF) or dichloromethane, working at a temperature between −70° C. e 100° C., preferably between −25° C. and 25° C., more preferably between −20° C. and 5° C.

In accordance with the present invention, the compound of formula (I) can be obtained, for example, by adding NH$_3$ gas, NH$_3$ in aqueous solution or in organic solvent as defined above, or a salt of NH$_3$, selected from those defined above, preferably (NH$_4$)$_2$CO$_3$, in a solution of the compound of formula (II) in an aprotic solvent as defined above, preferably acetone, working at temperatures preferably between −25° C. and 25° C.

The conversion of a compound of formula (I) to dorzolamide and its hydrochloride salt can be obtained by means of application of the known synthesis steps already presented for example in Schema 1, using the compound of formula (I) as raw material instead of the corresponding racemate and following the method illustrated in Schema 3:

Schema 3

Dorzolamide Cloridrato

The scope of the present invention therefore includes the preparation of the compound of formula (IV) as defined above, for example in step (i) of Schema 3, which comprises the oxidation of the compound of formula (I) obtained by means of the process according to the present invention.

The scope of the present invention also includes the preparation of a compound of formula (V) as defined for example in step (ii) of Schema 3, which comprises the reduction of the carbonyl group of the compound of formula (IV) obtained by means of the process described above.

The scope of the present invention also includes the preparation of a compound of formula (VI) as defined above for example in step (iii) of Schema 3, which comprises the transformation of a compound of formula (V) obtained via the Ritter reaction by means of the process described above.

The scope of the present invention also includes the preparation of a compound of formula (VII) as defined for example in step (iv) of Schema 3, which comprises the reduction of a compound of formula (VI) obtained by means of the process described above.

The scope of the present invention also includes the preparation of the compound of formula (VIII) as defined for example in step (v) in Schema 3, which comprises the salification of a compound of formula (VII) obtained by means of the process described above.

The scope of the present invention also includes the preparation of the compound of formula (IX) as defined for example in step (vi) of Schema 3, which comprises treating with a base the compound of formula (VIII) obtained by means of the process described above.

The scope of the present invention additionally includes the preparation of dorzolamide hydrochloride as defined for example in step (vii) in Schema 3, which comprises treating with HCl the compound of formula (IX) obtained by means of the process described above. The compound of formula (II) is commercially available and can be prepared by methods known in the art. For example, the compound of formula (II) can be prepared by reacting the compound of formula:

with chlorosulfonic acid and thionyl chloride at temperatures between 0° C. and 40° C. in mass or in the presence of a solvent compatible with the reagents used, such as chlorinated solvents.

In a specific aspect, the present invention relates to the compound of formula (I) in its crystalline form 1 (form 1). The compound of formula (I) form 1 crystallizes in the space group P1 with cell parameters a=7.925 (2), b=7.927 (3), c=9.326 (3) Å, α=99.50° (3), β=101.09° (3), γ=102.31° (3) and V=548.6 Å3, with two independent molecules (Z'=2).

Figure 1:
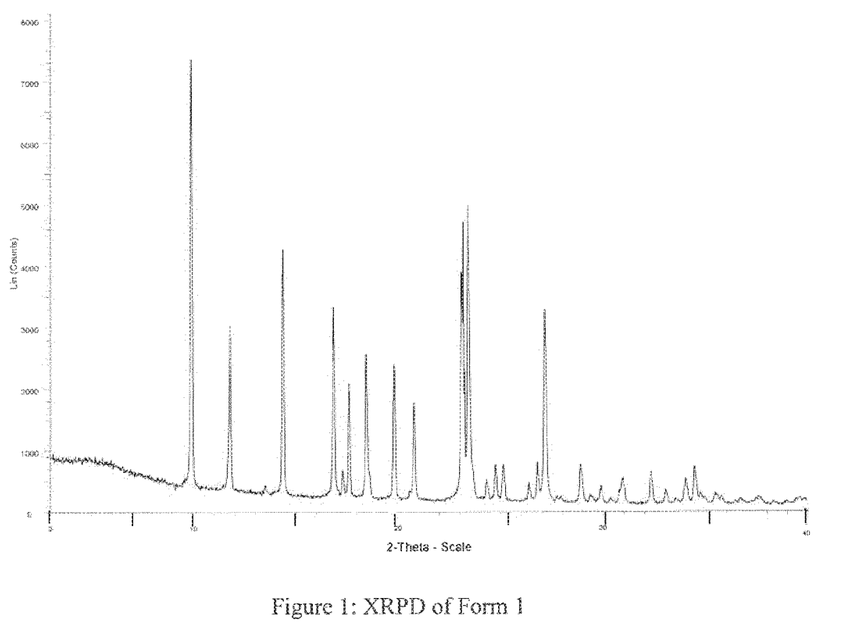
FIG. 1: XRPD for the crystalline form 1 (form 1) of the compound of formula (I).

The compound of formula (I) is characterised by the X-ray powder diffraction (more commonly known in the scientific field by the term XRPD) graph as illustrated in FIG. 1.

The characteristic peaks in XRPD of the compound of formula (I) are described in Table 1.

TABLE 1

| XRPD of the crystalline form 1 (form 1) of the compound of formula (I) | |
|---|---|
| 2 theta degrees (+0.1) | Relative intensity (Angstrom) |
| 9.865 | 8.959 |
| 23.443 | 3.793 |
| 14.359 | 6.164 |
| 23.133 | 3.842 |
| 16.837 | 5.261 |
| 27.181 | 3.278 |

In a further specific aspect, the present invention relates to the compound of formula (I) in its crystalline form 2. The compound of formula (I) form 2 crystallizes in the space group monocline P21 with cell parameters a=5.1447 (4) b=18.248 (1) c=11.847 (1) Å, β=95.494 (8), and V=1107.09 Å$^3$, with two independent molecules (Z'=2).

Figure 2:
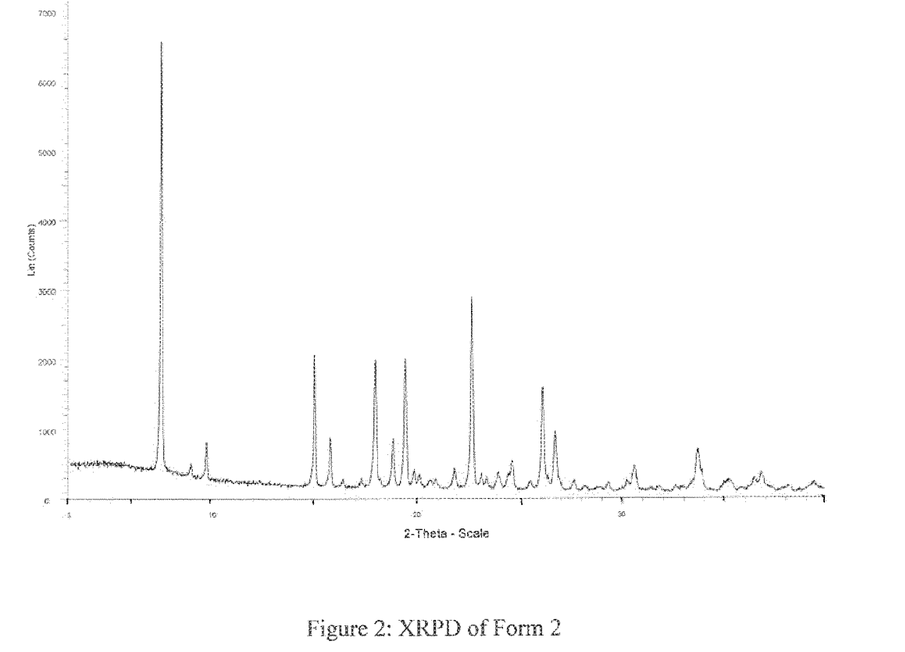
FIG. 2: XRPD for the crystalline form 2 (form 2) of the compound of formula (I).

The compound of formula (I) form 2 is characterised by the XRPD graph as illustrated in FIG. 2.

The characteristic peaks in XRPD of the compound of formula (I) are described in Table 2.

TABLE 2

| XRPD of the crystalline form 2 (form 2) of the compound of formula (I) | |
| --- | --- |
| 2 theta degrees (+0.1) | Relative intensity (Angstrom) |
| 7.491 | 11.792 |
| 15.007 | 5.899 |
| 17.959 | 4.935 |
| 19.425 | 4.556 |
| 22.652 | 3.922 |
| 26.122 | 3.409 |

According to the present invention, the compound of formula (I) form 1 can be prepared by purifying or isolating from the reaction environment the compound of formula (I) obtained by means of the process of the present invention, in the presence of solvents, such as acetone, water, THF, s-butanol, n-heptane, acetonitrile and mixtures thereof.

According to the present invention, the compound of formula (I) form 2 can be obtained by purifying or isolating from the reaction environment the compound of formula (I) obtained by means of the process according to the present invention, in the presence of solvents such as dichloromethane, water, acetonitrile and mixtures thereof.

The present invention will be illustrated further by means of the examples below.

EXAMPLES

Example 1

Synthesis of (6S)-5,6-dihydro-6-methyl-4H-thieno[2,3-b]thiopyran-4-one-2-sulfonamide Compound of formula (I)

Thionyl chloride (38.9 g, 326.6 mmol) was added to a mixture of chlorosulfuric acid (79.7 g, 683.9 mmol) at 4° C. under nitrogen in 10 minutes. The mixture was brought to 32° C., stirred at this temperature for 3 hours, and cooled in 1 hour to −3° C. 5,6-dihydro-4H—(S)-6-methylthieno[2,3-b]thiopyran-4-one (20.1 g, 109.2 mmol) was added in portions to the mixture. After this addition, the mixture was heated to 28° C. and left under stirring at this temperature for 10 hours. Once fully converted, the mixture was diluted with dichloromethane (250 mL) and quenched over demineralised water (876 mL) at 1° C. under nitrogen atmosphere. The organic phase was separated, the aqueous phase counter-extracted with dichloromethane (147 g), and the organic phases were combined (482 g). A portion of the organic phase (353.0 g) was concentrated under residual vacuum and diluted with acetone (82.8 g). The solution was concentrated again under vacuum and diluted with acetone (83.7 g).

Ammonia (18.55 g, solution 7 N in methanol, 161.2 mmol) was added to the obtained mixture of (S)-6-methyl-4-oxo-5,6-dihydro-4H-thieno[2,3-b]thiopyran-2-sulfonyl chloride (21.2 g, 75.0 mmol) in acetone (107 mL) at −10° C. under nitrogen atmosphere. Once the reaction was complete, the mixture was quenched with sulfuric acid (5.6 g, 1M aqueous solution) at −10° C. Demineralised water (163.6 g) was then added dropwise, whilst maintaining the temperature below 5° C. The temperature was brought to 0° C. and the mixture left under stirring at 0° C. for 6 hours and 30 min. The solid was then filtered and washed with demineralised water at 5° C. (39 mL) and dried to give (6S)-5,6-dihydro-6-methyl-4H-thieno[2,3-b]thiopyran-4-one-2-sulfonamide (16.6 g, titre 93.7%, ee 97%).

1H NMR: δH (ppm) (400 MHz; DMSO-d6) 7.8 (2H, s, SO2NH2), 7.65 (1H, s, CH), 4.1-4.0 (1H, m, CH), 2.9-2.8 (1H, m, CH2) 2.8-2.7 (1H, m, CH2), 1.39 (3H, d, J=7 Hz, CH3).

Example 2

(6S)-5,6-dihydro-6-methyl-4H-thieno[2,3-b]thiopyran-4-one-2-sulfonamide) Compound of formula (I)

Ammonium carbonate (19.02 g, 198.0 mmol) was added to a mixture of (S)-6-methyl-4-oxo-5,6-dihydro-4H-thieno[2,3-b]thiopyran-2-sulfonyl chloride (14.0 g, 49.5 mmol) in acetone (65 g) at 0° C. under nitrogen atmosphere. The mixture was stirred for 26 hours, then, once the reaction was complete, sulfuric acid (110.8 g of a 1M solution) was added at 0° C. After 3 additional hours, the precipitate was filtered and washed with demineralised water (27 mL) and dried to give (6S)-5,6-dihydro-6-methyl-4H-thieno[2,3-b]thiopyran-4-one-2-sulfonamide (8.26 g, titre 92.3%, ee 96%).

1H NMR: δH (ppm) (400 MHz; DMSO-d6) 7.8 (2H, s, SO$_2$NH$_2$), 7.65 (1H, s, CH), 4.1-4.0 (1H, m, CH), 2.9-2.8 (1H, m, CH$_2$) 2.8-2.7 (1H, m, CH$_2$), 1.39 (3H, d, J=7 Hz, CH$_3$).

Example 3

(6S)-5,6-dihydro-6-methyl-4H-thieno[2,3-b]thiopyran-4-one-2-sulfonamide Compound of formula (I) form 2

Ammonium hydroxide (2.3 g, 39.98 mmol, aqueous solution 29.6%) was added dropwise to a mixture of (S)-6-methyl-4-oxo-5,6-dihydro-4H-thieno[2,3-b]thiopyran-2-sulfonyl chloride (4.13 g, 14.61 mmol) in dichloromethane (16.5 g) at −10° C. under nitrogen atmosphere. The mixture was stirred for 19 hours, then the precipitate was filtered and washed with demineralised water (14.8 mL) and dried to give (6S)-5,6-dihydro-6-methyl-4H-thieno[2,3-b]thiopyran-4-one-2-sulfonamide (2.3 g, titre 86.8%, ee 96%).

1H NMR: δH (ppm) (400 MHz; DMSO-d6) 7.8 (2H, s, SO$_2$NH$_2$), 7.65 (1H, s, CH), 4.1-4.0 (1H, m, CH), 2.9-2.8 (1H, m, CH$_2$) 2.8-2.7 (1H, m, CH$_2$), 1.39 (3H, d, J=7 Hz, CH$_3$).

Example 4

(6S)-5,6-dihydro-6-methyl-4H-thieno[2,3-b]thiopyran-4-one-2-sulfonamide Compound of formula (I) form 1

Carbon (150 mg) was added to a solution of (6S)-5,6-dihydro-6-methyl-4H-thieno[2,3-b]thiopyran-4-one-2-sulfonamide (5.0 g, 91.1%, 17.3 mmol) in acetone (45.0 g) at 50° C. under nitrogen atmosphere. The mixture was stirred for 2 hours, then filtered and diluted with demineralised water (40.0 mL). The temperature was brought to 5° C. and the solid was filtered, washed with demineralised water (7.0 g) and dried to give (6S)-5,6-dihydro-6-methyl-4H-thieno[2,3-b]thiopyran-4-one-2-sulfonamide (3.95 g, titre 97.7%, ee 94%).

1H NMR: δH (ppm) (400 MHz; DMSO-d6) 7.8 (2H, s, SO$_2$NH$_2$), 7.65 (1H, s, CH), 4.1-4.0 (1H, m, CH), 2.9-2.8 (1H, m, CH$_2$) 2.8-2.7 (1H, m, CH$_2$), 1.39 (3H, d, J=7 Hz, CH$_3$).

Example 5

(6S)-5,6-dihydro-6-methyl-4H-thieno[2,3-b]thiopyran-4-one-2-sulfonamide Compound of formula (I) form 1

Carbon (100 mg) was added to a mixture of (6S)-5,6-dihydro-6-methyl-4H-thieno[2,3-b]thiopyran-4-one-2-sulfonamide (3.0 g, 93.7%, 10.7 mmol) in s-butanol (27.0 g) at 70° C. under nitrogen atmosphere. The mixture was stirred for 2 hours, then filtered and cooled to 5° C. The solid was filtered, washed with s-butanol at 5° C. (2 g) and dried to give (6S)-5,6-dihydro-6-methyl-4H-thieno[2,3-b]thiopyran-4-one-2-sulfonamide (1.98 g, titre 98.6%, ee 95%).

1H NMR: δH (ppm) (400 MHz; DMSO-d6) 7.8 (2H, s, $SO_2NH_2$), 7.65 (1H, s, CH), 4.1-4.0 (1H, m, CH), 2.9-2.8 (1H, m, $CH_2$) 2.8-2.7 (1H, m, $CH_2$), 1.39 (3H, d, J=7 Hz, $CH_3$).

Example 6

(6S)-4-oxo-5,6-dihydro-6-methyl-7,7-dioxo-4H-thieno[2,3-b]thiopyran-2-sulfonamide Compound of formula (IV)

Oxygenated water (2.2 g, titre 35.9%, 23.23 mmol) was added to a suspension of (S)-5,6-dihydro-6-methyl-4H-thieno[2,3-b]thiopyran-4-one-2-sulfonamide (2.0 g, 7.48 mmol) and sodium tungstate dihydrate (78 mg, 0.54 mmol) in methanol (8.3 g) under nitrogen atmosphere at 20° C. in one hour via measuring syringe. After this dropwise addition, the mixture was brought to 25° C. and was left under stirring for 24 hours. More oxygenated water (0.55 g, 35.9%, 5.76 mmol) was added to this mixture, and, after 6 hours, more sodium tungstate dihydrate (98 mg, 0.30 mmol). The mixture was left under stirring at 30° C. for 3 hours, then heated to 50° C. for 8 hours and lastly cooled to 15° C. The heterogeneous mixture stirred at 15° C. for 6 hours was cooled to 10° C. and the residual oxidative power was destroyed with a solution of sodium metabisulfite (5.4 g, 20% aqueous solution w/w). The mixture was diluted with methanol (7.9 g) and demineralised water (10.0 g) and then concentrated under vacuum up to a residual volume of 10 mL. The temperature was brought to 15° C., and the solid was filtered and washed with demineralised water (6.9 g in two portions), then dried to give (6S)-4-oxo-5,6-dihydro-6-methyl-7,7-dioxo-4H-thieno[2,3-b]thiopyran-2-sulfonamide (1.4 g, titre 96.8%, ee 96%).

1H NMR: δH (ppm) (400 MHz, DMSO-d6, 25° C.) 8.2 (2H, bs, $SO_2NH_2$), 7.8 (1H, m, CH), 4.5 (1H, m, CH), 2.5 (1H, s, CH), 1.4 (3H, d, J=7 Hz, $CH_3$).

Example 7 cis-(6S)-4-hydroxy-5,6-dihydro-6-methyl-7,7-dioxo-4H-thieno[2,3-b]thiopyran-2-sulfonamide Compound of formula (V)

Sodium borohydride (2.41 g, aqueous solution stabilised at 24%, 15.3 mmol) was added to a suspension of (6S)-4-oxo-5,6-dihydro-6-methyl-7,7-dioxo-4H-thieno[2,3-b]thiopyran-2-sulfonamide (13.2 g, 44.7 mmol) in THF (52.6 g) at 15° C. under nitrogen atmosphere in 1 hour via measuring syringe. The reactive mixture was stirred for 1 hour at 15° C. and then quenched with acetic acid (2.83 g). After this addition, the mixture was heated to 40° C. and was stirred at this temperature for 2 hours. The mixture was then concentrated at reduced pressure up to a volume of 20 mL and was then diluted with demineralised water (37.9 g). Distillation was continued up to a volume of 50 mL and the temperature was then set to 15° C. The solid was filtered and washed with demineralised water (29 g in 4 portions), then dried to give cis-(6S)-4-hydroxy-5,6-dihydro-6-methyl-7,7-dioxo-4H-thieno[2,3-b]thiopyran-2-sulfonamide (11.4 g, titre cis+trans 99.1%, de 96%, ee cis 99%).

1H NMR: δH (ppm) (400 MHz, DMSO, 25° C.) 8.0 (2H, bs, $SO_2NH_2$), 7.6 (1H, s, CH), 6.1 (1H, bs, OH), 4.8 (1H, bs, CH), 3.84 (1H, m, CH), 2.4 (1H, m, $CH_2$) 2.15 (1H, m, $CH_2$), 1.37 (3H, d, J=7 Hz, $CH_3$)

Example 8 trans-(6S)-4-acetylammino-5,6-dihydro-6-methyl-7,7-dioxo-4H-thieno[2,3-b]thiopyran-2-sulfonamide Compound of formula (VI)

Methanesulfonic acid (26.0 g, 270.5 mmol) was added dropwise to a suspension of cis-(6S)-4-hydroxy-5,6-dihydro-6-methyl-7,7-dioxo-4H-thieno[2,3-b]thiopyran-2-sulfonamide (23.0 g, 77.34 mmol) in acetonitrile (29.3 g) at 20° C. under nitrogen atmosphere in 20 minutes. The mixture was then diluted with acetonitrile (7.4 g) and heated to 87° C. After 15 hours under reflux, the temperature was lowered to 30° C., and after 3 hours to 10° C. Demineralised water (60.1 g) was added to the mixture at 10° C. in 30 minutes. The pH was then adjusted to 7.3 with ammonium hydroxide (16.0 g, 30% aqueous solution). The temperature was brought to 40° C. and the mixture was stirred at this temperature for 30 min. Demineralised water (60.0 g) was added to the mixture at 40° C. in 1 hour. The slurry was then stirred for 30 min at 40° C. and then cooled at 7° C. for a further 2 hours. The solid was filtered and washed with demineralised water (17.2 g, in 2 portions) and with isopropanol (17.2 g in 2 portions), then dried to give trans-(6S)-4-acetylamino-5,6-dihydro-6-methyl-7,7-dioxo-4H-thieno[2,3-b]thiopyran-2-sulfonamide (20.6 g, titre cis+trans 91.1%, de 58%).

Trans diastereoisomer: 1H NMR: δH (ppm) (400 MHz, DMSO) 8.6 (1H, m, NH), 8.0 (2H, bs, $SO_2NH_2$), 7.4 (1H, s, CH), 5.2 (1H, m, CH), 3.9 (1H, m, CH), 2.45 (1H, m, $CH_2$), 2.30 (1H, m, $CH_2$), 1.9 (3H, s, $COCH_3$), 1.37 (3H, s, J=7 Hz, $CH_3$).

Example 9

Synthesis of trans-(6S)-4-ethylamino-5,6-dihydro-6-methyl-7,7-dioxo-4H-thieno[2,3-b]thiopyran-2-sulfonamide maleate salt Compound of formula (VII) and (VIII)

Borane THF (176.9 g, 1M solution in THF) was added dropwise to a suspension of trans-(6S)-4-acetylamino-5,6-dihydro-6-methyl-7,7-dioxo-4H-thieno[2,3-b]thiopyran-2-sulfonamide (20.0 g, 59.1 mmol) in THF (36.7 g) at 38° C. under nitrogen atmosphere in 7 hours. The mixture was left under stirring at 38° C. for 10 hours and was then transferred to a solution of diluted hydrochloric acid at 60° C. The quench suspension was diluted with THF (19.5 g) and stirred under reflux for 1.5 hours. The mixture was then cooled, purified and diluted with THF (41.5 g) and demineralised water (18.7 g). The mixture was concentrated up to a volume of 100 mL, the pH adjusted to 7.5, and lastly the mixture was diluted with ethyl acetate (200.8 g). The aqueous phase was separated and counter-extracted with ethyl acetate (22.7 g).

The combined organic phases were washed with demineralised water (17.5 g) and then concentrated under vacuum to a volume of approximately 30 mL. The mixture was then diluted with ethyl acetate (142.6 g) and concentrated to a volume of approximately 30 mL. ⅓ of the solution was subjected to a change of solvent with acetone (102.2 g) by distilling repeatedly up to 10 g of residues. The residue was diluted with acetone (16.0 g), and maleic acid (6.6 g, 20% solution in acetone) was added to the mixture at 40° C. After the addition process, the temperature was brought to 20° C., the solid was filtered and washed with acetone (8.2 g, in 2 portions), then dried to give trans-(6S)-4-ethylamino-5,6-dihydro-6-methyl-7,7-dioxo-4H-thieno[2,3-b]thiopyran-2-sulfonamide maleate salt (4.4 g, titre trans+cis 88.3%, de 99.6%, ee 99.9%).

1H NMR: δH (ppm) (400 MHz, DMSO) 8.2 (2H, bs, $SO_2NH_2$), 7.8 (1H, s, CH), 6.05 (2H, CH═CH), 4.6 (1H, bs, CH), 4.0 (1H, m, CH), 3.2 (1H, m, ½ AB, NH—$CH_2$), 3.0 (1H, m, ½ AB, NH—$CH_2$), 2.7-2.5 (2H, m, $CH_2$), 1.4 (3H, d, J=7 Hz, $CH_3$), 1.2 (3H, m, $CH_3$).

Example 10

(4S,6S)-4-(ethylamino)-5,6-dihydro-6-methyl-4H-thieno[2,3-b]thiopyran-2-sulfonamide-7,7-dioxide, monochloride Dorzolamide Hydrochloride Sodium hydroxide (8.0 g, 30% aqueous solution) was added to a suspension of trans-(6S)-4-ethylamino-5,6-dihydro-6-methyl-7,7-dioxo-4H-thieno[2,3-b]thiopyran-2-sulfonamide maleate salt (12.0 g, 27.2 mmol) in water (35 mL) at 52° C. under nitrogen atmosphere. The pH was adjusted to 7.7 with hydrochloric acid (2.3 g, 31.5% aqueous solution) and the mixture was diluted with ethyl acetate (36.1 g). The phases were separated and the aqueous phase counter-extracted with ethyl acetate (24.8 g). The phases were separated and the combined organic phases were washed with water (10.2 g) and concentrated up to a volume of approximately 30 mL. The mixture was then diluted with isopropyl alcohol (26.5 g) and the distillation process continued. The residue was diluted with isopropyl alcohol (33.0 g), and hydrochloric acid (4.6 g, 31.5% aqueous solution) was added to the mixture at 75° C. The temperature was brought to 20° C., the solid was filtered and washed with isopropyl alcohol (14.6 g, in 2 portions), then dried to give (4S,6S)-4-(ethylamino)-5,6-dihydro-6-methyl-4H-thieno[2,3-b]thiopyran-2-sulfonamide-7,7-dioxide, monochloride (8.1 g, titre 99.2%, ee 100%).

1H NMR: δH (ppm) (400 MHz, DMSO) 9.9 (bs, 1H, —$NH_2^+Cl^-$), 9.6 (bs, 1H, —$NH_2^+Cl^-$), 8.2 (s, 2H, $SO_2NH_2$), 8.0 (s, 1H, CH), 4.7 (bs, 1H, CH), 4.35 (m, 1H, CH), 3.2 (bs, 1H, NH—$CH_2$), 3.0 (bs, 1H, NH—$CH_2$), 2.8 (m, 1H, $CH_2$), 2.6-2.5 (m, 1H, $CH_2$), 1.4 (d, 3H, J=6 Hz, $CH_3$), 1.3 (t, 3H, J=7 Hz, $CH_3$).

The invention claimed is:
1. A compound of formula (I):

(I)

2. A crystalline form 1 (form 1) of the compound of formula (I) as described in claim 1, characterised by an X-ray powder diffraction (XRPD) graph having 2 theta peak values at 9.865; 23.443; 14.359; 23.133; 16.837 and 27.181.

3. The form 1 according to claim 2, having XRPD as described in FIG. 1.

4. A crystalline form 2 (form 2) of the compound of formula (I) as described in claim 1, characterised by an X-ray powder diffraction (XRPD) graph having 2 theta peak values at 7.491; 15.007; 17.959; 19.425; 22.652 and 26.122.

5. The form 2 according to claim 4, having XRPD as described in FIG. 2.

6. A process for preparing the compound of formula (I) as described in claim 1 with an enantiomeric excess equal to or greater than 60%

(I)

comprising the step of reacting the compound of formula (II)

(II)

with NH3 or salts thereof; said process being characterised in that the reaction is carried out in an acidic or neutral environment.

7. The process according to claim 6, wherein the acidic or neutral reaction environment is obtained by reacting one mole equivalent of the compound of formula (II) with an amount between 2 and 3 mole equivalents of NH3.

8. The process according to claim 6, wherein NH3 gas or NH3 in organic solution is used.

9. The process according to claim 6, said process being carried out in an organic solvent selected from the group consisting of methanol, ethanol, isopropanol and dioxane, in the presence of a polar or non-polar aprotic solvent, selected from the group consisting of acetone, tetrahydrofuran (THF) and dichloromethane.

10. The process according to claim 9, said process being carried out working at a temperature between −70 ° C. and 100 °C.

11. A process for preparing a compound of formula (IV)

(IV)

comprising oxidizing the compound of formula (I), obtained in accordance with the process according to claim 6.

12. A process for preparing a compound of formula (V)

(V)

comprising reducing the carbonyl group of the compound of form (IV), obtained in accordance with the process according to claim 11.

13. A process for preparing a compound of formula (VI)

(VI)

comprising transforming the compound of formula (V), obtained in accordance with the process according to claim 12.

14. A process for preparing a compound of formula (VII)

(VII)

comprising reducing a compound of formula (VI), obtained in accordance with the process according to claim 13.

15. A process for preparing a compound of formula (VIII)

(VIII)

comprising salifying with maleic acid a compound of formula (VII) obtained in accordance with the process according to claim 14.

16. A process for preparing a compound of formula (IX)

(IX)

DOROZOLAMIDE comprising the step of treating with a base the compound of formula (VIII) obtained in accordance with the process according to claim 15 and, where necessary, salifying dorzolamide with HCl to obtain the corresponding hydrochloride salt.

* * * * *